(12) United States Patent
Hsieh et al.

(10) Patent No.: US 8,761,478 B2
(45) Date of Patent: *Jun. 24, 2014

(54) SYSTEM AND METHOD FOR TOMOGRAPHIC DATA ACQUISITION AND IMAGE RECONSTRUCTION

(75) Inventors: Jiang Hsieh, Brookfield, WI (US); Brian Edward Nett, Madison, WI (US); Debashish Pal, Waukesha, WI (US); Basel Hasan Taha, Madison, WI (US); Jean-Baptiste Thibault, Milwaukee, WI (US); Zhou Yu, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 421 days.

This patent is subject to a terminal disclaimer.

(21) Appl. No.: 12/775,308

(22) Filed: May 6, 2010

(65) Prior Publication Data

US 2011/0142315 A1    Jun. 16, 2011

Related U.S. Application Data

(63) Continuation-in-part of application No. 12/638,723, filed on Dec. 15, 2009, now Pat. No. 8,280,137.

(60) Provisional application No. 61/314,937, filed on Mar. 17, 2010.

(51) Int. Cl.
*G06K 9/00* (2006.01)
*G06K 9/46* (2006.01)
*A61B 6/00* (2006.01)

(52) U.S. Cl.
USPC ............. 382/131; 382/128; 382/195; 378/4

(58) Field of Classification Search
USPC ......... 382/131, 128, 130, 132, 168, 190, 206, 382/219, 254, 263, 305, 195; 378/4, 5, 6, 7, 378/8, 9, 10, 11, 12, 13, 14, 15, 16, 17, 18, 378/19, 20, 101, 109, 110, 111, 112, 114, 378/115, 901

See application file for complete search history.

(56) References Cited

U.S. PATENT DOCUMENTS 5,860,927 A    1/1999  Sakaguchi et al.
6,483,892 B1   11/2002 Wang et al.

(Continued)

FOREIGN PATENT DOCUMENTS

EP    1959397 A2    8/2008
WO   2004010383 A2  1/2004

(Continued)

OTHER PUBLICATIONS

Chen et al., "Temporal resolution improvement using PICCS in MDCT cardiac imaging," Medical Physics, vol. 36, No. 6, Jun. 2009, pp. 2130-2135.

(Continued)

*Primary Examiner* — Sheela Chawan
(74) *Attorney, Agent, or Firm* — Ziolkowski Patent Solutions Group, SC

(57) ABSTRACT

A tomographic system includes a gantry having an opening for receiving an object to be scanned, a radiation source, a detector positioned to receive radiation from the source that passes through the object, and a computer. The computer is programmed to acquire a plurality of projection datasets of the object, define a temporal subset of projection datasets from the plurality of projection datasets, reconstruct a working image of the object using the plurality of projection datasets, identify a region of motion in the working image, and minimize motion artifacts in the region of motion in the working image using the temporal subset of projection datasets.

30 Claims, 9 Drawing Sheets

(56) References Cited

U.S. PATENT DOCUMENTS

| | | |
|---|---|---|
| 6,614,874 B2 | 9/2003 | Avinash |
| 6,661,873 B2 | 12/2003 | Jabri et al. |
| 6,792,072 B2 | 9/2004 | Avinash |
| 6,841,998 B1 | 1/2005 | Griswold |
| 6,934,357 B2 | 8/2005 | Boyd et al. |
| 6,950,689 B1 | 9/2005 | Willis et al. |
| 7,054,475 B2 * | 5/2006 | Edic et al. .............. 382/131 |
| 7,068,826 B2 | 6/2006 | Jabri et al. |
| 7,221,728 B2 | 5/2007 | Edic et al. |
| 7,289,049 B1 | 10/2007 | Fudge et al. |
| 7,330,027 B2 | 2/2008 | Kozerke et al. |
| 7,358,730 B2 | 4/2008 | Mistretta et al. |
| 7,408,347 B2 | 8/2008 | Mistretta et al. |
| 7,519,412 B2 | 4/2009 | Mistretta |
| 7,545,901 B2 | 6/2009 | Mistretta |
| 7,558,414 B2 | 7/2009 | Griswold |
| 7,613,275 B2 | 11/2009 | Li et al. |
| 7,647,088 B2 | 1/2010 | Mistretta et al. |
| 7,750,304 B2 | 7/2010 | Wang |
| 7,778,381 B2 * | 8/2010 | Nishide et al. .............. 378/4 |
| 7,792,347 B2 | 9/2010 | Manzke et al. |
| 8,131,043 B2 | 3/2012 | Binkley et al. |
| 2004/0136490 A1 | 7/2004 | Edic et al. |
| 2004/0174960 A1 | 9/2004 | Hsieh et al. |
| 2006/0029279 A1 | 2/2006 | Donoho |
| 2006/0257012 A1 | 11/2006 | Kaufman et al. |
| 2007/0010731 A1 | 1/2007 | Mistretta |
| 2007/0038073 A1 | 2/2007 | Mistretta |
| 2007/0049817 A1 | 3/2007 | Preiss et al. |
| 2007/0106149 A1 | 5/2007 | Mistretta |
| 2007/0156044 A1 | 7/2007 | Mistretta et al. |
| 2007/0167707 A1 | 7/2007 | Mistretta et al. |
| 2007/0167728 A1 | 7/2007 | Mistretta et al. |
| 2007/0167729 A1 | 7/2007 | Mistretta et al. |
| 2008/0170654 A1 | 7/2008 | Tkaczyk et al. |
| 2008/0199063 A1 | 8/2008 | O'Halloran et al. |
| 2008/0219535 A1 | 9/2008 | Mistretta et al. |
| 2008/0304728 A1 | 12/2008 | Licato et al. |
| 2009/0076369 A1 | 3/2009 | Mistretta |
| 2009/0129651 A1 | 5/2009 | Zagzebski et al. |
| 2009/0161932 A1 | 6/2009 | Chen |
| 2009/0161933 A1 | 6/2009 | Chen |
| 2009/0175523 A1 | 7/2009 | Chen et al. |
| 2009/0274355 A1 | 11/2009 | Chen et al. |
| 2010/0128958 A1 | 5/2010 | Chen et al. |
| 2010/0310144 A1 | 12/2010 | Chen et al. |

FOREIGN PATENT DOCUMENTS

| | | |
|---|---|---|
| WO | 2006003578 A1 | 1/2006 |
| WO | 2006064401 A2 | 6/2006 |
| WO | 2008047268 A1 | 4/2008 |

OTHER PUBLICATIONS

Nett et al., "Temporally Targeted Imaging Method Applied to ECG-Gated Computed Tomography: Preliminary Phantom and In Vivo Experience," Academic Radiology, vol. 15, No. 1, Jan. 2008, pp. 93-106.

Qiao et al., "Region of interest motion compensation for PET image reconstruction," Physics in Medicine and Biology, vol. 52, 2007, pp. 2675-2689.

Schretter et al., "Local correction of non-periodic motion in computed tomography," Proceedings of SPIE, vol. 7258, Jan. 1, 2009, pp. 1-12.

Linney et al., "Organ Motion Detection in CT Images Using Opposite Rays in Fan-Beam Projection Systems," IEEE Transactions on Medical Imaging, vol. 20, No. 11, Nov. 2001, pp. 1109-1122.

Chen et al., "Prior image constrained compressed sensing (PICCS): A method to accurately reconstruct dynamic CT images from highly undersampled projection data sets," Medical Physics Author Manuscript, pp. 1-8, Published in final edited form as: Medical Physics, vol. 35, No. 2, Feb. 2008, pp. 660-663.

Chen et al., "Prior image constrained compressed sensing (PICCS)," Proc Soc Photo Opt Instrum Eng. Author Manuscript, pp. 1-34, Published in final edited form as: Proc Soc Photo Opt Instrum Eng., Mar. 3, 2008; 6856: 685618. doi:10.1117/12.770532.

Nett et al., "Tomosynthesis via Total Variation Minimization Reconstruction and Prior Image Constrained Compressed Sensing (PICCS) on a C-arm System," Proc Soc Photo Opt Instrum Eng. Author Manuscript, pp. 1-14, Published in final edited form as: Proc Soc Photo Opt Instrum Eng., Mar. 18, 2008; 6913: nihpa92672. doi:10.1117/12.771294.

Fessler et al., "Iterative Image Reconstruction in MRI With Separate Magnitude and Phase Regularization," pp. 1-4, Apr. 15-18, 2004.

Lustig et al., "Rapid MR Imaging with 'Compressed Sensing' and Randomly Under-Sampled 3DFT Trajectories," Stanford University, p. 1, Jun. 5, 2006.

Donoho, "Compressed Sensing," Sep. 14, 2004, pp. 1-34.

Mistretta et al., "Highly constrained backprojection for time-resolved MRI," Abstract, Magnetic Resonance in Medicine, vol. 55, No. 1, Jul. 20, 2005, pp. 30-40.

Schmidt, "Least Squares Optimization with L1-Norm Regularization," Dec. 2005, pp. 1-12.

Lustig et al., "Compressed Sensing MRI," Stanford University, Technical Report No. 2007-3, Jul. 2007, pp. 1-40.

Song et al., "Sparseness prior based iterative image reconstruction for retrospectively gated cardiac micro-CT," Published in final edited form as: Med Phys., vol. 34, No. 11, Nov. 2007, pp. 4476-4483.

O'Halloran et al., "Iterative Projection Reconstruction of Time-Resolved Images Using Highly-Constrained Back-Projection (HYPR)," Magnetic Resonance in Medicine, vol. 59, 2008, pp. 132-139.

Search Report and Written Opinion from corresponding EP Application No. 10192855.4, dated Apr. 7, 2011.

* cited by examiner

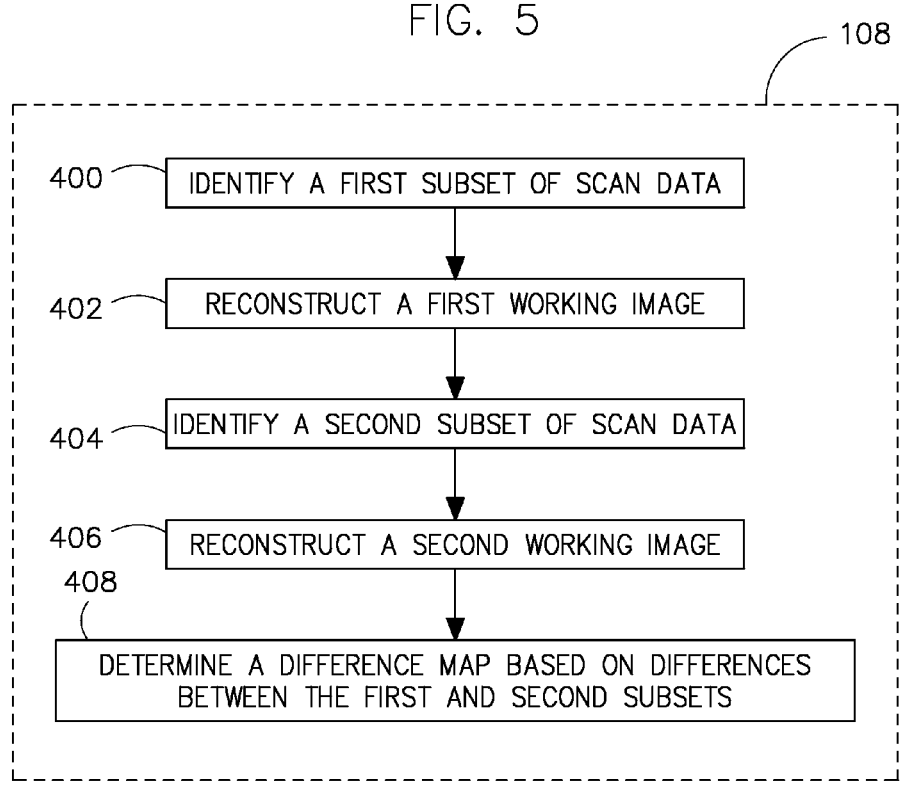
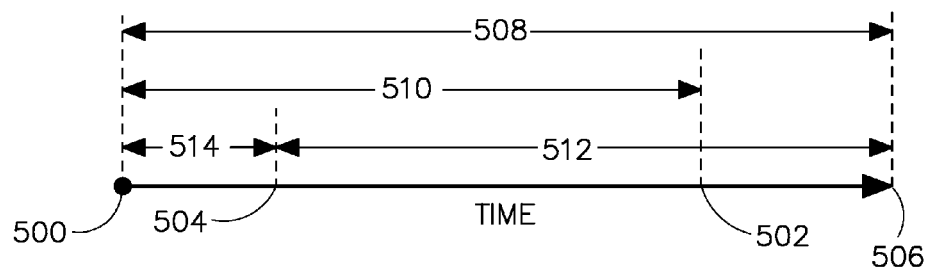

SYSTEM AND METHOD FOR TOMOGRAPHIC DATA ACQUISITION AND IMAGE RECONSTRUCTION

CROSS-REFERENCE TO RELATED APPLICATION

The present application claims priority to U.S. Provisional Application 61/314,937 filed Mar. 17, 2010, and the present application is a continuation-in-part of and claims priority to U.S. patent application Ser. No. 12/638,723 filed Dec. 15, 2009, the disclosures of which are incorporated herein.

BACKGROUND OF THE INVENTION

Embodiments of the invention relate generally to tomographic imaging and, more particularly, to an apparatus and method of acquiring tomographic imaging data and reconstructing a tomographic image having improved temporal resolution.

Typically, in x-ray systems, such as computed tomography (CT) imaging systems, an x-ray source emits a fan-shaped or cone-shaped beam toward a subject, such as a patient, a piece of luggage, or any other object of interest. Hereinafter, the terms "subject" and "object" shall include anything capable of being imaged. The beam, after being attenuated by the subject, impinges upon an array of radiation detectors. The intensity of the attenuated beam of radiation received at the detector array is typically dependent upon the attenuation of the x-ray beam by the subject. Each detector element of the detector array produces an electrical signal indicative of the attenuated beam received by the detector element. The electrical signals are converted to digital signals and transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam from a focal point. X-ray detectors typically include a collimator for collimating x-ray beams directed toward the detector, a scintillator adjacent to the collimator for converting x-rays to light energy, and photodiodes for receiving the light energy from the scintillator and producing electrical signals therefrom. Typically, each scintillator of a scintillator array converts x-rays to light energy and discharges the light energy to a photodiode adjacent thereto. Each photodiode detects the light energy and generates a corresponding electrical signal. The outputs of the photodiodes are digitized and then transmitted to the data processing system for image reconstruction. The x-ray detector extends over a circumferential angular range or fan angle, often typically 60°.

The general terminology "CT imaging" encompasses multiple configurations. For example, configurations can include a multi-slice imaging system or a multi-detector CT (MDCT) imaging system, as examples, which may be employed for cardiac imaging. Such a system may be used to generate a cardiac image using imaging data that is obtained over a portion or phase of a cardiac cycle. Conventionally, the minimum projection angle of imaging data for image reconstruction is 180° of gantry rotation plus the x-ray detector fan angle. Thus, with a typical fan angle of 60°, the minimum projection angle or temporal aperture is 240° of projection data for image reconstruction. This projection data is said to be obtained over a "half-scan" or "short scan" range of coverage and may be reconstructed using known reconstruction techniques. The amount of time taken to obtain this half-scan projection dataset together with the reconstruction algorithm, in this conventional example, defines the temporal resolution of the imaging system. In other words, the temporal resolution is defined as the time taken to obtain minimally adequate data for image reconstruction and the data actually used in the reconstruction. In one case, short scan data is obtained for 240° of gantry rotation with some type of weighting function, as is understood in the art.

The range of angular coverage (or temporal aperture) and gantry rotational speed are thus primary factors that define temporal resolution in an MDCT scanner. In a typical single source MDCT scanner, temporal resolution is thus approximately 135 ms for a gantry rotational speed of 270 ms, and approximately 175 ms for a gantry rotational speed of 350 ms with a Parker-type weighting, for example. In many imaging applications, such temporal resolution is adequate to provide images with acceptable motion artifacts.

Due to motion of the heart during the 240° of gantry rotation when this short scan data is acquired however, the temporal resolution may be inadequate in that the images reconstructed with short scan data can suffer from blurring, streaking, or other imaging artifacts. This is due, fundamentally, to motion of the heart that occurs during this 240° acquisition, based on typical heart rates, gantry speeds, and the like. However, a quiescent period of the cardiac cycle occurs during approximately 90° to 130° of gantry rotation. It is desirable to increase temporal resolution in cardiac imaging applications, and in applications in general, where imaging artifacts may occur due to object motion over 240° of gantry rotation. It would be desirable to increase temporal resolution by a factor of up to 2, or even greater, based on typical heart rates, in order to improve images and reduce or eliminate image artifacts.

Temporal resolution could be improved by increasing the gantry speed and thereby decreasing overall acquisition time or modifying the hardware, such as adding additional sources and detectors. Artifacts may be reduced or eliminated because reconstruction occurs using data obtained over a smaller time period.

However, the gantry weight and other forces acting on the gantry limit the speed at which the gantry can operate. As is known in the art, load on the gantry increases generally as a factor that is squared with respect to gantry rotational speed. Therefore, after certain speeds, further reduction in the acquisition time typically requires more powerful x-ray tubes in order to achieve improved image quality. Thus there are life, reliability, and performance considerations to take into account, and it is highly nontrivial to maintain stability and functionality of components on the gantry at increased gantry speeds.

Another technique to improve temporal resolution includes a dual-tube/detector configuration. In such a system, two tubes operate simultaneously, thus decreasing overall acquisition time and increasing the temporal resolution as compared to a single source system. While resolution is improved, it comes with an associated increased that can be prohibitive. In addition, space limitations on the gantry can restrict placement of two x-ray tubes and two full-FOV detectors in a single compact gantry. Thus, the second detector often covers only a fraction of the desired scan FOV. Further, a dual-tube/detector CT system can include significantly more utility resources (i.e., coolant flow, electrical) when compared to a single tube system.

Thus, imaging suites containing such systems sometimes need significant and costly upgrades to provide additional the additional utility resources. Additionally, with an increased number of operational components, reliability of the overall system may be compromised because of the doubling in the number of primary components (i.e., tube, detector, and DAS). Thus, though such a system may improve temporal resolution, the increased temporal resolution comes at the cost of increased initial system expense and cost of ongoing operation, costly upgrades, and possibly reduced reliability when compared to a single source system.

It is also known that other imaging modalities, such as single photon emission computed tomography (SPECT) and positron emission tomography (PET), can also benefit from increased resolution to improve blurring and other image artifacts due to cardiac or respiratory motions. Such blurring may be caused by inadequate data acquisition during a given acquisition, or may be caused by an inordinate amount of time to obtain tomographic imaging data.

Thus there is a need for a system and method that minimizes motion blurring in tomographic imaging in a cost-effective and overall efficient manner without the added costs associated with doubling the hardware.

BRIEF DESCRIPTION OF THE INVENTION

Embodiments of the invention are directed to a method and apparatus for acquiring imaging data and reconstructing an image having an improved temporal resolution.

According to one aspect of the invention, a tomographic system includes a gantry having an opening for receiving an object to be scanned, a radiation source, a detector positioned to receive radiation from the source that passes through the object, and a computer. The computer is programmed to acquire a plurality of projection datasets of the object, define a temporal subset of projection datasets from the plurality of projection datasets, reconstruct a working image of the object using the plurality of projection datasets, identify a region of motion in the working image, and minimize motion artifacts in the region of motion in the working image using the temporal subset of projection datasets.

According to another aspect of the invention, a method of image reconstruction includes obtaining a plurality of projection datasets of an object, defining a temporal subset of projection datasets from the plurality of projection datasets, reconstructing an image of the object using the plurality of projection datasets, and correcting a motion artifact in at least one identified voxel of the image using the temporal subset of projection datasets.

According to yet another aspect of the invention, a computer readable storage medium having stored thereon a computer program comprising instructions, which, when executed by a computer, cause the computer to access a plurality of tomographic view datasets of an object, identify a temporal subset of the plurality of tomographic view datasets, reconstruct a processing image of the object using the plurality of tomographic view datasets, and revise at least one image voxel in an identified region of motion of the processing image using at least one tomographic view dataset of the temporal subset of tomographic view datasets.

These and other advantages and features will be more readily understood from the following detailed description of embodiments of the invention that is provided in connection with the accompanying drawings.

BRIEF DESCRIPTION OF THE DRAWINGS

FIG. 5 is a flowchart depicting a technique for identifying motion in scan data according to an embodiment of the invention.

FIG. 6 is an exemplary time line depicting exemplary time periods associated with the technique of FIG. 5.

DETAILED DESCRIPTION

Tomographic imaging devices comprise x-ray systems, magnetic resonance (MR) systems, ultrasound systems, computed tomography (CT) systems, positron emission tomography (PET) systems, ultrasound, nuclear medicine, single photon emission computed tomography (SPECT) systems, X-ray systems having a C-arm, and other types of imaging systems. Applications of x-rays can comprise various imaging, inspection, and analysis applications including in the fields of medicine, security, and industrial inspection applications. Embodiments of the invention herein will be described with respect to tomographic imaging systems that include, at least, CT, SPECT, and PET. However, it is to be understood that embodiments of the invention are generally applicable to any imaging system, such as an X-ray system, in which data is reconstructed from a temporal window in which data outside of the temporal reconstruction window may be available and employed to improve image reconstruction and reduce blurring and other artifacts therein.

Cardiac coronary imaging can be successfully performed at high heart rates (e.g., greater than 90 beats per minute) according to embodiments of the invention. For instance, temporal resolution of cardiac CT imaging can be effectively improved by approximately a factor of 2 without modifying any scanner hardware versus traditional techniques. Thus, embodiments of the invention include a single-source MDCT scanner that can achieve reliable coronary CT imaging of patients at heart rates higher than the current and conventional heart rate limit of 70 bpm. Embodiments of the invention also allow, for instance, a dual-source MDCT scanner to achieve even higher temporal resolution without hardware modifications versus a dual-source MDCT scanner not using embodiments of the invention. Associated improvements in SPECT and PET temporal resolution are achieved as well.

Figure 1:
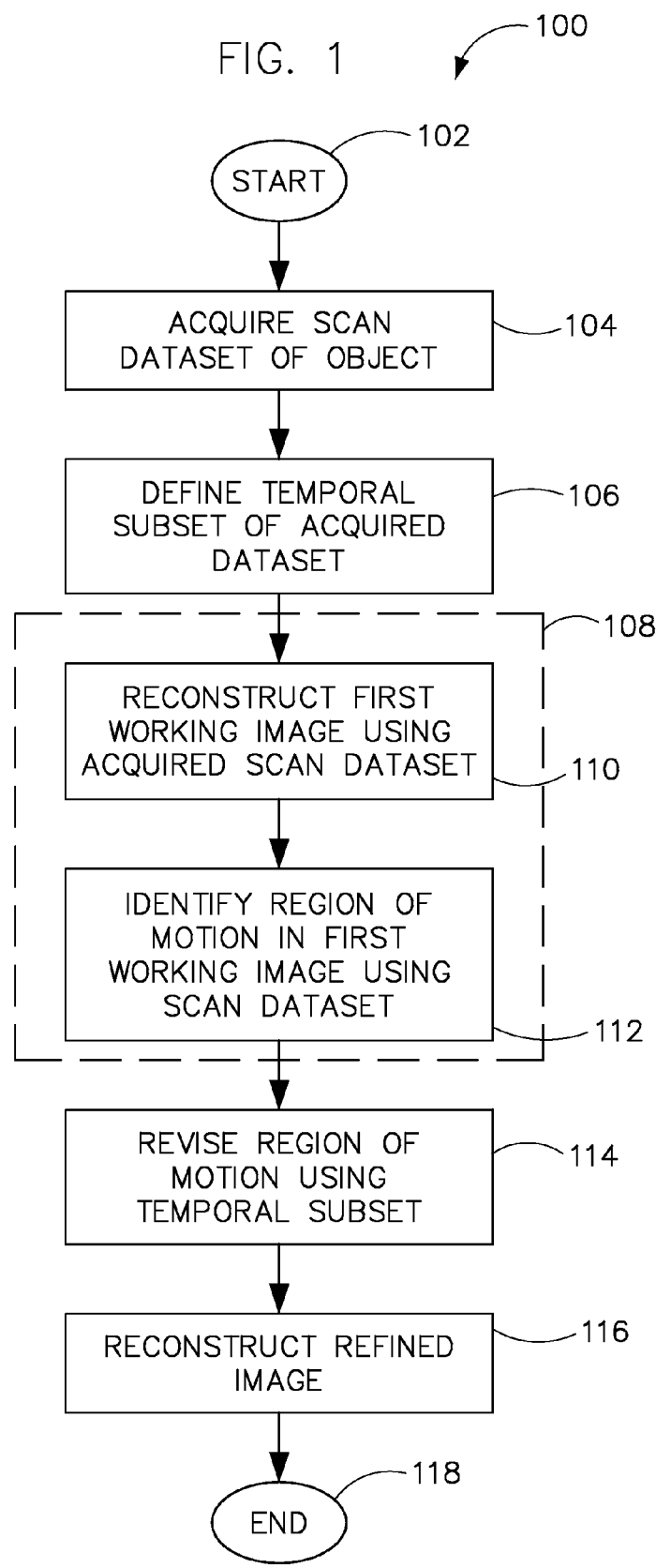
FIG. 1 is a flowchart general to tomographic imaging systems illustrating data acquisition and image reconstruction, according to embodiments of the invention.

FIG. 1 is a flowchart general to many tomographic imaging systems illustrating data acquisition, image reconstruction, and image refinement to obtain improved temporal resolution of images, according to embodiments of the invention. Thus, in general and according to embodiments of the invention, a technique 100 includes reconstructing an image and refining the image to improve the temporal resolution thereof. Technique 100 starts at step 102 where scan data is acquired of an object, which typically includes a plurality of projection datasets 104 over a given temporal range or during a period that may be particular for the given imaging system. For example, for CT imaging at step 104 a short-scan dataset may be acquired, which, as understood in the art, typically comprises 180° plus a detector angle of gantry rotation. However, embodiments of the invention are not to be so limited, and at step 104, greater than a short scan of data may be acquired. According to another example, at step 104, scan data is obtained that is in excess of the defined short-scan range of gantry motion. For SPECT, the data may be obtained over a period of, for instance, 10 minutes and over 180° of gantry rotation. For PET, imaging data may be obtained over, for example, a 5 minute period.

However, as stated, images reconstructed using data acquired over these acquisition periods may have poor temporal resolution and may have motion artifacts in regions thereof. Thus, embodiments of the invention include identifying regions of motion (or image voxels having motion) in an image reconstructed therefrom, and revising the regions of motion using a temporally reduced subset of the acquired data. A subset of the acquired data is defined temporally from the plurality of projection datasets at step 106. In the case of CT, the temporal subset of acquired data ranges from approximately 90° to 130° of gantry rotation and is approximately 120° in one embodiment. For SPECT, a temporally reduced subset of the acquired dataset is defined that includes a fraction of the acquired dataset having a desired temporal distribution. For PET, likewise, a temporally reduced subset of data is defined for image reconstruction.

Steps for identifying motion in the acquired data or for generating a motion map are represented by dashed box 108. The steps within box 108 include reconstructing a first processing or working image at step 110 using the scan dataset or a subset thereof that was acquired at step 104. As understood in the art, the first working image may be reconstructed by any number of known techniques that include but are not limited to a model-based iterative reconstruction (MBIR), an algebraic reconstruction technique (ART), a simultaneous algebraic reconstruction technique (SART), an ordered subset expectation maximization (OSEM), and a kinetic parameter iterative reconstruction (KPIR). At step 112, regions of motion in the first working image are identified using the scan dataset, according to embodiments of the invention. As will be illustrated and discussed in further detail, one or more regions of motion may be identified in the first working image using image or projection data. Once the one or more regions of motion are identified, the identified one or more regions of motion may be revised using the defined temporal subset of data at step 114. After the revision of the region(s) of motion at step 114, a refined image is reconstructed at step 116, and technique 100 ends at step 118.

Following is a description and illustration of technique 100 as it applies to a CT scanner. However, as stated and as will be illustrated, technique 100 applies equally to other imaging modalities that include but are not limited to SPECT and PET.

Figure 2:
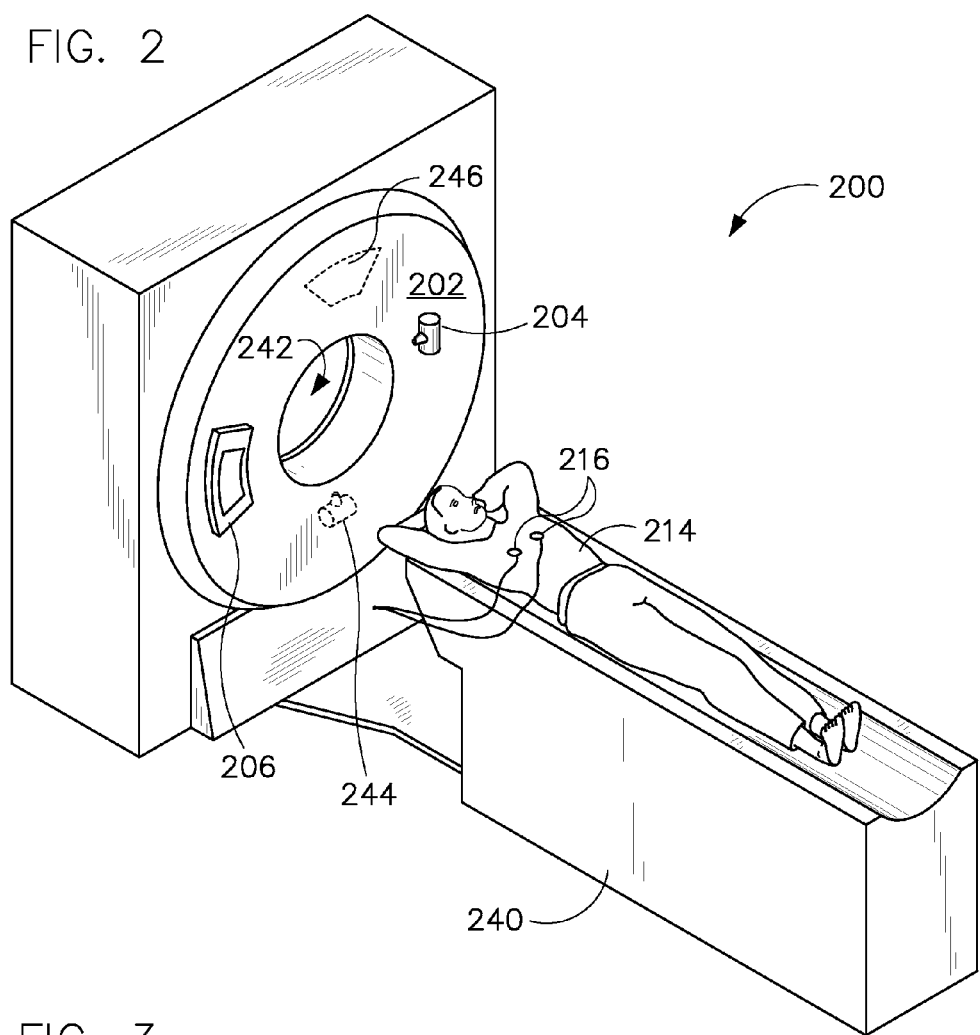
FIG. 2 is a pictorial view of a CT imaging system incorporating embodiments of the invention.
Figure 3:
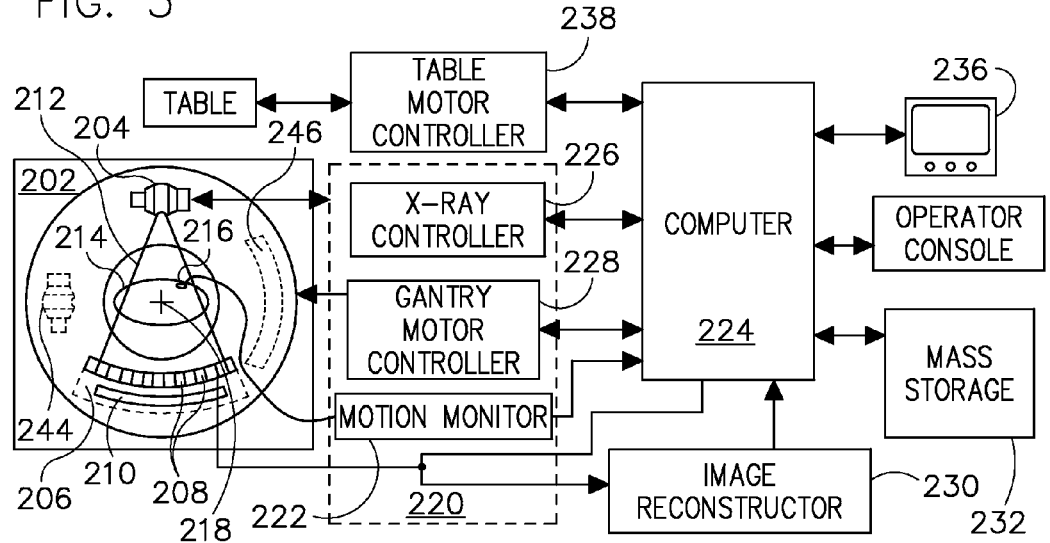
FIG. 3 is a block schematic diagram of the system illustrated in FIG. 1 incorporating embodiments of the invention.

FIGS. 2 and 3 illustrate, respectively, a pictorial view of a CT system 200 and a schematic block diagram thereof. Referring to FIG. 2, CT imaging system 200 is shown as including a gantry 202 representative of a "third generation" CT scanner. Gantry 202 has an x-ray source 204 that projects a beam of x-rays toward a detector assembly 206 on the opposite side of gantry 202. Referring now to FIG. 3, detector assembly 206 is formed by a plurality of detectors 208 and a data acquisition systems (DAS) 210. The plurality of detectors 208 sense projected x-rays 212 that pass through a medical patient 214 having, in one embodiment, a motion monitor 216, such as an electrocardiographic (ECG) device, is attached thereto. DAS 210 converts data from plurality of detectors 208 to digital signals for subsequent processing. Each detector 208 produces an analog electrical signal that represents the intensity of an impinging x-ray beam and hence the attenuated beam as it passes through medical patient 214. During a scan to acquire x-ray projection data, gantry 202 and the components mounted thereon rotate about a center of rotation 218.

Rotation of gantry 202 and operation of x-ray source 204 are governed by a control mechanism 220 of CT imaging system 200. In one embodiment, control mechanism 220 includes a motion monitoring system 222 configured to acquire data from motion monitor 216 and pass patient motion information to a computer 224. Examples of the patient motion information include respiratory and cardiac phase information. Control mechanism 220 includes an x-ray controller 226 that provides power and timing signals to x-ray source 204 and a gantry motor controller 228 that in turn, controls a rotational speed and position of gantry 202. An image reconstructor 230 receives sampled and digitized x-ray data from data acquisition systems (DAS) 210 and performs high speed reconstruction. The reconstructed image is applied as an input to computer 224, which stores the image in a mass storage device 232.

Computer 224 also receives commands and scanning parameters from an operator via an operator console 234 that includes an operator interface, such as a keyboard, mouse, voice activated controller, or any other suitable input apparatus. An associated display 236 allows the operator to observe the reconstructed image and other data from computer 224. The operator supplied commands and parameters are used by computer 224 to provide control signals and information to data acquisition systems (DAS) 210, x-ray controller 226 and gantry motor controller 228. In addition, computer 224 operates a table motor controller 238 which controls a motorized table 240 to position medical patient 214 and gantry 202. Particularly, motorized table 240 moves medical patient 214 through a gantry opening 242 of FIG. 2 in whole or in part. In one embodiment, CT imaging system 200 includes a second x-ray source 244 and a corresponding second detector assembly 246 positioned to receive x-rays passing through medical patient 214 in order to obtain additional imaging data. The second source/detector combination 244/246 may be controlled and used to obtain imaging data similarly to that illustrated with respect to x-ray source 204 and detector assembly or collimator 206 and may be used, for instance, to improve the overall temporal resolution of CT imaging system 200 while incorporating embodiments of the invention.

According to embodiments of the invention, motion in cardiac tomography images can be reduced or eliminated using projection data acquired over a CT gantry angular range of 90°-130°, and in approximately 120° in one embodiment. As a result, the temporal resolution of MDCT cardiac imaging can be universally improved by approximately a factor of 2 when compared to an image reconstructed using a conventional short-scan data acquisition. Embodiments of the invention include using approximately half of the acquired short-scan CT data to improve temporal resolution in the first working image. As stated, the short-scan angular range is approximately 180° plus a detector fan angle of gantry rotation, or 240° for a detector fan angle of 60°. This is typically believed to be a minimal data sufficiency condition to reconstruct an entire cross section within a scanning field of view using conventional CT reconstruction techniques. When the cardiac window is narrowed to half of the short-scan window, the available ~120° angular range normally does not enable accurate image reconstruction, and images reconstructed therefrom suffer from limited view-angle shading artifacts. Thus, without additional information, this type of image reconstruction raises classical tomosynthetic reconstruction issues that usually do not have an algorithm to enable accurate image reconstruction.

However, as stated with respect to FIG. 1, images having improved resolution may be reconstructed according to embodiments of the invention. Half-scan data is used to reconstruct a first working image, which is an angular range of 240° and typically 600-700 view angles. A temporal subset of the short-scan data is defined and used from 90°-130° of the short scan data, or approximately 300-350 view angles. The first working image may be reconstructed from the half-scan data by any number of known techniques that include but are not limited to a model-based iterative reconstruction (MBIR), an algebraic reconstruction technique (ART), a simultaneous algebraic reconstruction technique (SART), an ordered subset expectation maximization (OSEM), and a kinetic parameter iterative reconstruction (KPIR).

Figure 4:
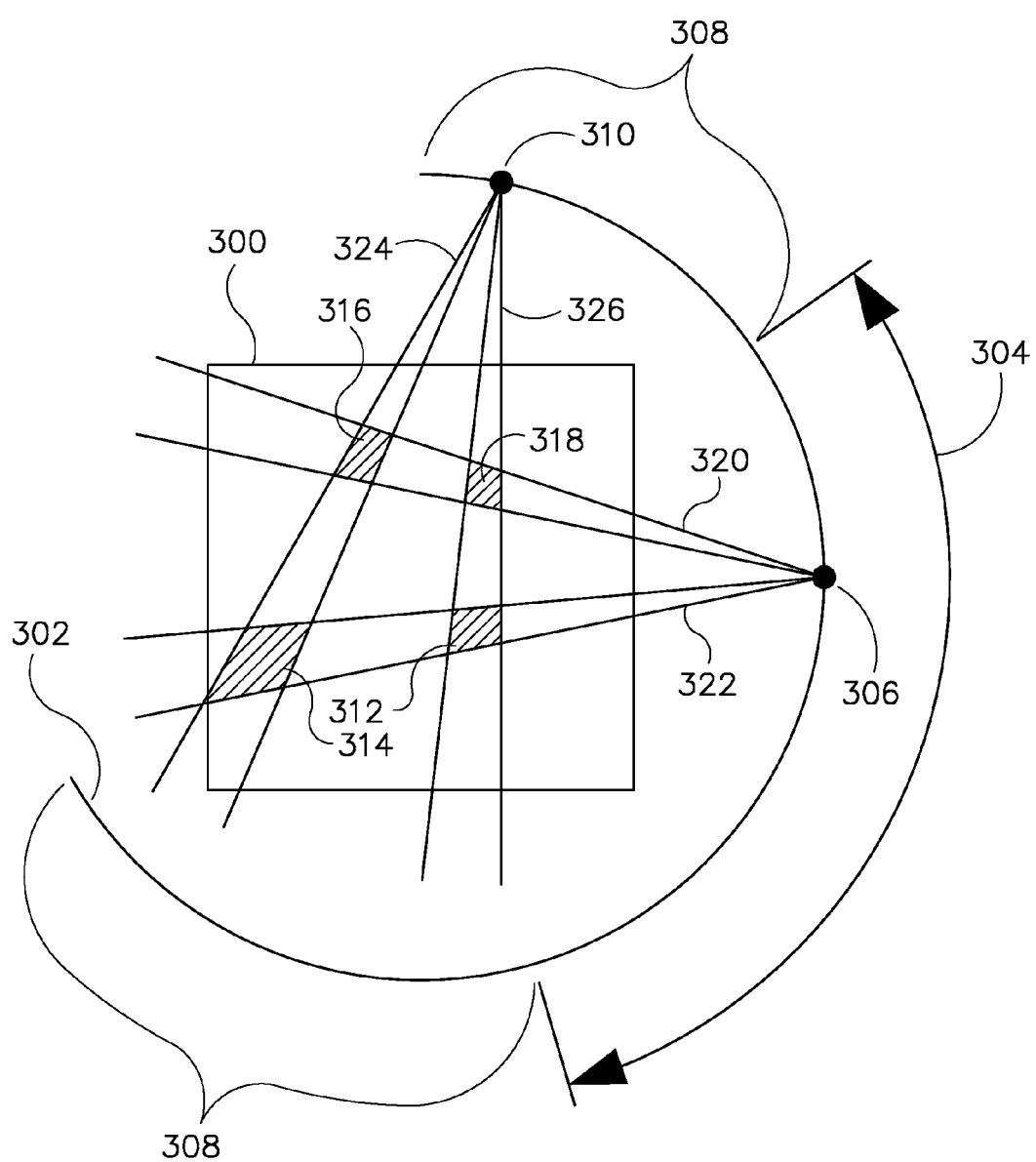
FIG. 4 is an illustration of half-scan data used to identify regions of motion in a working image, according to one embodiment of the invention.

Motion in the first working image may be identified by a number of means according to the invention. According to one embodiment, as illustrated in FIG. 4, the first working image may be assessed using the half-scan projection data to identify regions of motion, and the identified regions of motion can be corrected according to embodiments of the invention. According to other embodiments, as illustrated in FIGS. 5-8, subsets of projection data can be identified to generate a second working image, and from the first and second working images, motion may be identified and corrected.

Referring now to FIG. 4, a first working image 300 is reconstructed using known techniques from half-scan data acquired at step 104 of technique 100, and represented by step 110. An arc 302 illustrates data acquired over approximately 240° degrees of angular range used to reconstruct working image 300, thus arc 302 represents source positions of the typically 600-700 view angles of scan data acquired during a half-scan. From first working image 300, motion in the image may be identified by determining a temporal window during which little or no motion occurred, based on for instance data obtained using an ECG. A temporal subset of the acquired dataset is thus defined as image data obtained with a source positioned about a sub-arc 304 and comprised of 90°-130° of the short scan data, or approximately 300-350 view angles, which corresponds to step 106 of technique 100. Because projection data corresponding to sub-arc 304 is defined as a temporal subset, little or no motion has occurred during the acquisition of this data. Projection data acquired from source locations within sub-arc 304 and at, for instance, a first point 306 can thus be presumed to be during a quiescent period of the cardiac cycle. Thus, image data generated therefrom is assumed to have little or no motion.

However, because first working image 300 was generated using imaging data acquired over arc 302, motion in first working image 300 can be identified using projection data from arc 302 that is obtained outside of sub-arc 304 at regions 308. Thus, projection data acquired with a source location at a second point 310, for instance, may be used to identify regions of motion in first working image 300. In other words, if first working image 300 includes, for instance, four motion locations 312, 314, 316, and 318, then it can be assumed that the motion did not occur from projections 320 or 322 because projections 320 and 322 were acquired during the defined temporal window and during a quiescent period of the cardiac cycle. Rather, motion in locations 312-318 may be identified using projections 324, 326, if motion was indeed occurring in locations 312-318 while the source was at position 310. In fact, one skilled in the art will now recognize that motion in first working image 300 may be identified by synthesizing the typically 600-700 view angles of scan data acquired over arc 302. Thus, as stated with respect to technique 100 above, one or more regions of motion in the first working image may be identified at step 112 as discussed with respect to FIG. 4. As such, steps 108 of technique 100 include reconstructing a first working image 300 using imaging data acquired over arc 302, and identifying regions of motion in first working image 300 using projection datasets by synthesizing the acquired imaging data over arc 302 with the assumption that motion generated therein may be identified using projection data obtained outside the temporal window 304 and in regions 308.

Steps in dashed box 108 of technique 100 may generate a motion map of an image, according to other embodiments of the invention. In general, these embodiments include identifying first and second subsets of CT data, reconstructing working images therefrom, and mapping a difference between the two identified subsets to generate a motion map therefrom. Referring now to FIGS. 5 and 6, steps of box 108 of FIG. 1 are augmented as follows to identify regions of motion in the first working image. FIG. 5 illustrates identifying a first subset of the CT data at step 400, and a first working image may be generated therefrom at step 402. It is contemplated that approximately one half-scan or more worth of data is represented in the first subset of the CT data. Proceeding to step 404, a second subset of the CT data is identified, and a second working image may be generated therefrom at step 406. Similar to the first subset of the CT data, it is contemplated that approximately one half-scan or more worth of data is represented in the second subset of the CT data. A difference map may be generated at step 408 as will be described.

According to one embodiment, a scan dataset may be acquired that includes greater than a half-scan of data in order to identify a region of motion in a working image. Referring to FIG. 6, a first half-scan acquisition includes a first subset of CT data acquired from a start time 500 or slightly before or after start time 500 to a first half-scan end time 502, whereas a second half-scan acquisition includes a second subset of CT data acquired from a second half-scan start time 504 to stop time 506 or slightly before or after stop time 506. The portion of time period 508 ranging from start time 500 to first half-scan end time 502 can be referred to as a first subset time period 510 of time period 508, and the portion of time period 508 ranging from second half-scan start time 504 to stop time 506 can be referred to as a second subset time period 512 of time period 508. In this example, time period 508 corresponds to step 104 of FIG. 1.

Accordingly, the first subset of CT data includes CT data that was acquired over first subset time period 510, whereas the second subset of the CT data includes CT data that was acquired over second subset time period 512. As depicted in FIG. 6, first subset time period 510 overlaps a portion of second subset time period 512. As such, the first subset of CT data shares some common data with the second subset of CT data. It is contemplated, however, that this need not necessarily be the case. That is, it is contemplated first subset time period 510 and second subset time period 512 do not share common acquisitions in one embodiment. In such an embodiment, a first subset time period would not overlap a second subset time period.

Referring back to FIG. 5, after the second subset of the CT data is identified at step 404 and a second working image is reconstructed at step 406, process control proceeds to step 408, where a difference image or map is determined. The difference map identifies or locates one or more regions of motion within the object based on difference(s) between the first and second subsets of the CT data. Such differences may be determined in image space or projection space. For example, according to one embodiment of the invention employed in image space, a difference between a first image based on the first subset of the CT data and a second image based on the second subset of the CT data is determined. As a result, a difference or motion map is determined. The locations of non-zero values, or substantially non-zero values, in the motion map correspond to locations within the first and second images where object motion occurred during acquisition of the CT data. Conversely, the locations of zero values, or substantially zero values, correspond to location(s) in the first and second images where the object was static, or at least substantially static, during acquisition of the CT data.

Alternatively, according to another embodiment employed in projection space, differences between the first and second subsets of the CT data are determined in projections space. However, as with a motion map determined in image space, the differences determined in projection space also result in a motion map (i.e., a projection-domain motion map) where one or more regions of motion caused by a region within the object are identified or located. This projection-domain motion map can be referred back to the image domain (i.e., a difference image map) by, for example, performing a combination of known backprojection and thresholding operations.

Another approach in projection space can be to compute an error between projection data and a projection obtained from a forward projection of an image reconstructed using half-scan data. The motion map can be computed by a combination of a known backprojection of the error and a thresholding operation.

Another approach based on projection data can be to use KPIR to generate a motion map. KPIR in principal models voxels as time varying functions. Half-scan data can be reconstructed using KPIR, and the voxels with significant time-varying component can be considered in a motion mask, and a mask can generated by a simple thresholding operation.

Referring back to FIG. 1, after producing or determining motion in a working image or regions of motion from the motion map 112, process control proceeds to step 114, where image data that corresponds to the locations or regions of motion previously identified is iteratively updated via an iterative reconstruction technique. The image data corresponds to a first portion of the first subset of the CT data. As such, image data or voxels corresponding to a first portion of the first subset of the CT data, which corresponds to the locations of the one or more non-zero difference values, are updated via an iterative reconstruction technique.

It is noted that not all image data is iteratively updated. In other words, only image data that corresponds to the object motion located on the motion map is iteratively updated. Thus, image updating occurs in a more efficient manner. After updating a portion of the image data 114, process control proceeds to step 116, where a CT image is reconstructed from the iteratively updated image data and non-iteratively updated image data. It is noted that image voxels that are outside of the identified motion location(s) can be reconstructed using more than a half-scan of acquisitions, since motion effects are not as detrimental in such location(s).

Accordingly, as set forth in technique 100, CT image data that corresponds to locations in the object that suffered from motion effects are iteratively updated, whereas the CT image data corresponding to regions outside the located motion areas are not subjected to iterative reconstruction. Since the iteratively updated regions are isolated to only a portion of the image data corresponding to the first subset of the CT data set, fewer views can be used to formulate the final CT image. That is, only a portion of the image data corresponding to the defined temporal subset of data is used in the update process. As a result, image processing time is reduced since not all image data was subjected to such iterative reconstruction. Further, the resulting CT image has an increased temporal resolution relative to an image based on only un-updated image data since motion effects were removed or reduced. For example, if only one-half of the projection views are used to produce the final image, the temporal resolution can be improved by a factor of two.

The selection of the temporal subset is determined based on a motion pattern in the half-scan. The selection can be based on an image-space based algorithm or a projection-space based algorithm. The selection criterion can be global or local based on a location of the coronary arteries. The local approach will be vessel specific. In the image-space based approach, certain direction filters can be applied in a local region to estimate motion during the half-scan. The appropriate temporal subset can be determined based on the motion information. Approaches based on segmenting the vessels and tracking the movement of the vessel using multiple half-scan images may be used to determine the motion of the vessel, and in turn aid in the selection of the temporal subset with the given half-scan data.

In the projection-space based approach, a global metric may be determined by tracking a movement of a center-of-mass for each view or correlation between the views or a metric that is combination of multiple criterions. A quiescent temporal subset would be a phase with minimal movement of center-of-mass or highest correlation. A local approach can be also developed in projection space. In this case, a region in projection data corresponding to a particular vessel may be determined based on its location and similar metrics described above can be utilized to determine the quiescent temporal phase within the half-scan data.

It is noted that, instead of or in addition to updating image data corresponding to a first portion of the first subset of the CT data, image data corresponding a portion of the second subset of the CT data that corresponds to the locations identified via the motion map can be updated via an iterative reconstruction technique. In such an embodiment, the CT image having the increased temporal resolution would be reconstructed from the updated portion(s) of the image data corresponding to the second subset and the non-updated portion(s) of the image data corresponding to the second subset.

It is also contemplated that to further enhance the motion map created at step 408, high-pass filtering can be applied to first and/or second subsets of CT data in a direction parallel to a ray connecting the location of the source at the center-view and the iso-center. Accordingly, the high-pass filtering may reduce selection of undesirable pixels and/or allow a threshold to be reduced in order to allow pixels near small moving structures, such as coronaries, to be selected.

Embodiments of technique 100 may, for example, be implemented to reduce motion artifacts often present in a cardiac image. That is, a motion map may be determined to identify regions of motion in a cardiac region. For example, referring back to FIG. 6, it is contemplated that projection views acquired over first subset time period 510 may approximately correlate to a cardiac phase, whereas projection view acquired over second subset time period 512 may correlate with a different cardiac phase. Accordingly, technique 100 of FIG. 1 may be implemented to reduce cardiac artifacts that might otherwise be present in a cardiac image.

It is noted that the areas of motion detected by technique 100 may be dependent on a temporal offset between the two sets of projection views (i.e., the temporal offset between the first and second subsets of the CT data) used to generate the motion map. For example, referring again to FIG. 6, a temporal offset 514 between the projection views acquired over first subset time period 510 and second subset time period 512 may affect the magnitude of the non-zero values identified in the motion map as well as affecting the quantity of non-zero locations present in the motion map.

It is also contemplated that the local motion estimation may be improved by combining information from multiple motion maps created from a comparison of multiple sets of projection views with different offsets. As such, it is contemplated that technique 100 may be repeated one or more times to create additional motion maps. For instance, assume a full rotation of data is available over 0.5 seconds. Then a single half-scan image may be generated from 0.25 s worth of data. With a time offset of 50 ms (see e.g., offset 514 of FIG. 6) between the time windows (see e.g., first subset time period 510 and second subset time period 512), a total of six half-scan images and five motion maps, each depicting motion locations estimated from the temporal difference between uncorrelated projection views in each image with a particular angular focus, can be generated. The combination of the information in each motion map may provide an improved technique to estimate the sparse regions of local motion in the overall scanned object.

According to another embodiment, temporal offset 514 may be configured such that a "center view" of the projections associated with first subset time period 510 is substantially 180° apart from a center view of projections associated with second subset time period 512. As such, artifacts germane to the orientation of the motion relative to the angular coverage may be suppressed, thereby providing better identification of the location(s) of motion identified in the motion map. In such an embodiment, each of the first and second subsets of CT data may be represented by a root mean square (RMS) error image, respectively, that is low passed filtered.

According to another embodiment, a weighted difference of the acquired projection data associated with the first and second subsets of the CT data may be employed to increase computational efficiency, thus increasing the rate at which the temporally resolved CT image having reduced motion artifacts can be reconstructed. In such an embodiment, a back projection process can be carried out to produce the motion map.

Figure 7:
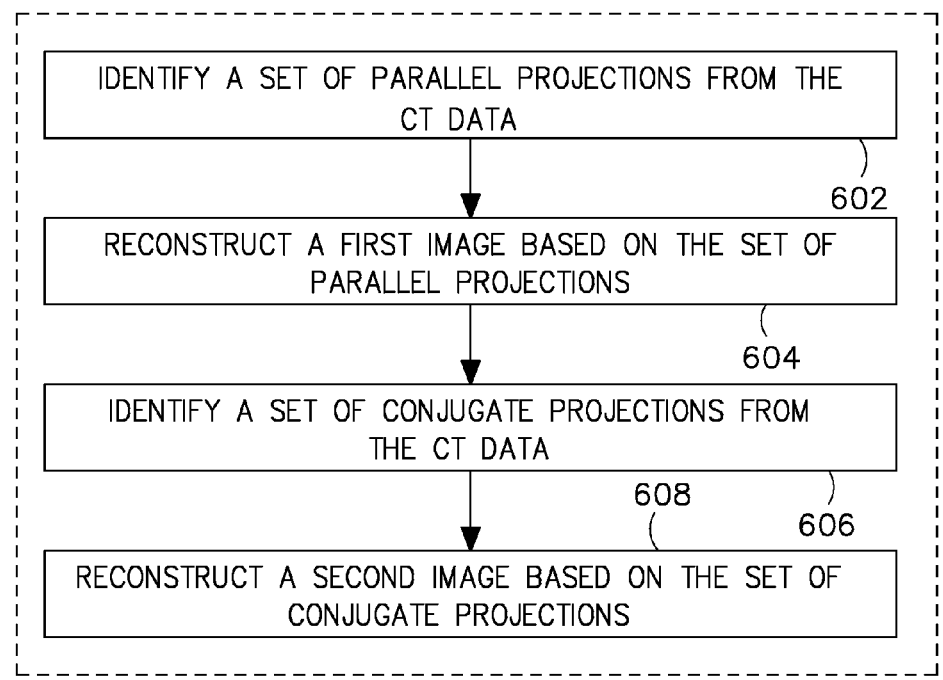
FIG. 7 is a flowchart depicting a technique for generating a motion map according to an embodiment of the invention.
Figure 8:
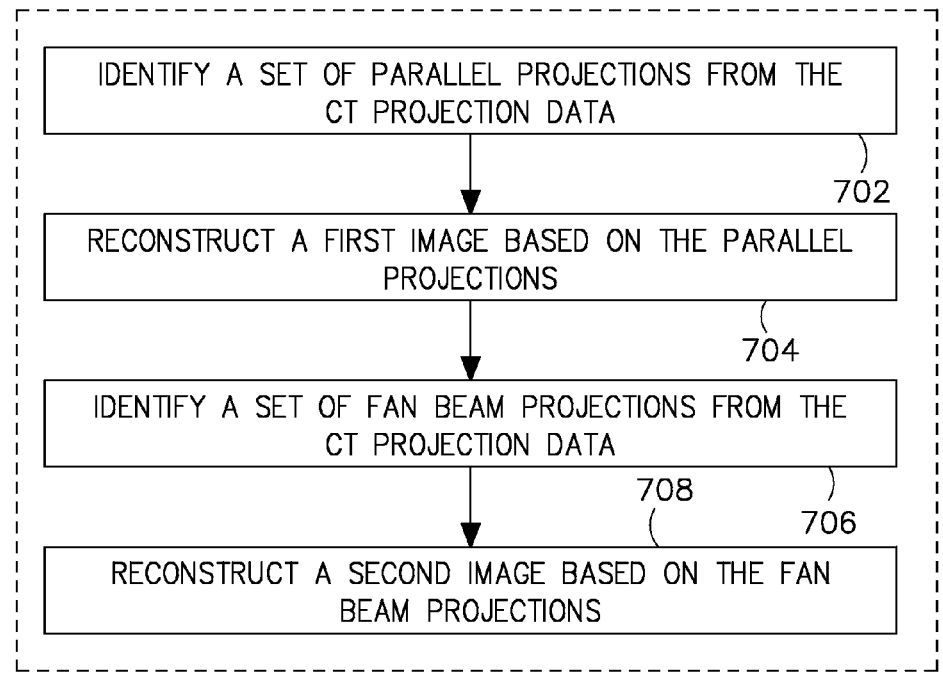
FIG. 8 is a flowchart depicting a technique for generating a motion map according to another embodiment of the invention.

As discussed above, a difference region or motion map can be determined either in projection space or image space. Accordingly, the generation of a motion map component represented by dashed box 108 can be carried out via a variety of embodiments. FIGS. 7-8 and the accompanying description thereof depict several embodiments of motion map generation.

Referring to FIG. 7, a flowchart depicting a technique 600 (corresponding to steps 400-406 of FIG. 5) for generating a motion map in image space is shown according to an embodiment of the invention. Technique 600 begins at step 602, where a set of parallel projections represented in the CT data are identified, thus representing the first subset of the CT data identified at step 400 of FIG. 5. It is contemplated that a technique such as fan-to-parallel beam rebinning may be implemented to identify the parallel projections represented in the CT data. Process control then proceeds to step 604 of FIG. 7, where a first image is reconstructed from the data corresponding to the identified parallel projections (i.e., the first subset of the CT data).

After the first image is reconstructed 604, CT data corresponding to conjugate projections are identified at step 606 using a technique such as a fan-to-parallel rebinning technique. These conjugate projections represent the second subset of the CT data identified at step 404 of FIG. 5. Process control then proceeds to step 608 of FIG. 7, where a second image based on the data representing the conjugate projections (i.e., the second subset of the CT data) is reconstructed. As such, according to technique 600, a first image based on parallel projections is reconstructed, and a second image based on conjugate projections is reconstructed. From the first and second images, a motion map can be determined.

Technique 600 of FIG. 7 depicts a sequence that proceeds from parallel projection data identification to first image reconstruction based on the parallel projection data, to conjugate projection data identification, and then to reconstruction of a second image based on the conjugate projection data. It is contemplated, however, that the order in which the acts (i.e., steps 602-608) of technique 600 are implemented may be varied. For example, reconstruction of the first image may occur after identification of the conjugate projection data or after the reconstruction of the second image.

Referring now to FIG. 8, a flowchart depicting a technique 700 (corresponding to steps 400-406 of FIG. 5) for generating a motion map in image space is shown according to an embodiment of the invention. Technique 700 begins at step 702, where a set of parallel projections represented in the CT data is identified, thus representing the first subset of the CT data discussed at step 400 of FIG. 5. Process control then proceeds to step 704 of FIG. 8, where a first image is reconstructed from the CT data that represents the identified parallel projections, thus reconstructing a parallel-beam CT image. It is contemplated that a view-based weighting function may be employed during such a reconstruction.

Process control then proceeds to step 706, where CT data representing fan-beam projections are identified from the CT projection data, thus representing the second subset of the CT data discussed at step 404 of FIG. 5. After identifying CT data representing fan-beam projections 706, a second image is reconstructed from the identified fan-beam projection CT data at step 708 of FIG. 8, thus reconstructing a fan-beam CT image. It is contemplated that a channel-and-view based weighting function may be employed during the reconstruction of the fan-beam CT image.

From the motion regions identified with respect to FIG. 4, or the parallel-beam CT image motion maps generated with respect to FIG. 7 or 8, the regions of motion may be revised (e.g., see step 114 of FIG. 1). In such embodiments, it is contemplated that portions of the motion map that are substantially non-zero are likely linked to the poorer temporal resolution of the parallel beam and, therefore, linked to the motion. It is contemplated that the order in which the acts (i.e., blocks 702-708 of FIG. 8) of technique 700 occur may be different than that shown in FIG. 8.

Still other embodiments for the determination of first and second CT images are contemplated. For example, phase and gantry motion may be manipulated such that conjugate views see little motion. In yet another embodiment, the determination of motion may be limited to one direction. For example, a determination of motion may be limited to a direction that is most susceptible to blur and artifacts, such as the direction perpendicular to the start and stop views of a half-scan. In yet another embodiment, a motion map is determined in projection space and the resulting motion map is the converted to image space.

As discussed above with respect to FIG. 1, an iterative reconstruction technique is employed to update the CT data based on region(s) of motion identified. Generally, an iterative reconstruction technique includes a minimization of a cost function formed by the sum of a data mismatch term and regularization terms. Iteratively reconstructed data may take on the following form:

$$\hat{x} = \underset{x \in \Omega}{\operatorname{argmin}} \{F(Ax, y) + \beta U(x)\}, \quad \text{(Eqn. 1)}$$

In Eqn. 1, "y" represents the acquired projection data, "x" represents the image, "A" represents a forward projection operator in a manner similar to the scanning operation of the CT system, "F(·)" represents a distortion measure that may include different degrees of confidence between the acquired data "y" and the set "Ax" of synthesized data according to the model of the CT system, and "$\Omega$" represents a convex set such as a set of non-negative images. Further, "$\beta U(\cdot)$" represents a regularization term over the image "x," where "$\beta$" represents a scaling factor to balance image quality and "U(·)" represents a cost function.

A cost function, such as "U(·)", typically includes a spatial component to improve noise and spatial resolution properties of the image. For example, "U(·)" may take the form of the following:

$$U_s(x) = \Sigma_k \Sigma_j b_{jk} \phi(x_j - x_k), \quad \text{(Eqn. 2),}$$

where "$\phi(\cdot)$" represents a potential function acting on local neighbor differences, and $b_{jk}$ represents a directional scaling coefficient.

Additional information may be introduced in the iterative reconstruction process to improve temporal resolution. For example, an additional temporal regularization factor may be employed to further improve temporal resolution. An expression having an additional temporal regularization factor is shown below:

$$\hat{x} = \arg\underset{x \in \Omega \cup \Phi}{\min} \{F(Ax, y) + \beta_s U_s(x) + \beta_t U_t(x)\}, \quad \text{(Eqn. 3)}$$

where $\beta_t U_t(x)$ represents the additional regularization term, $\Phi$ is the set of image voxels affected by motion according to the motion estimation, $U_s(\cdot)$ and $U_t(\cdot)$ represent cost functions, and the remaining variables generally comport with Eqn. 1. It is noted that an iterative coordinate descent approach, which performs individual voxel updates, is suited to realize such sparse updates, rather than a conjugate gradient approach or other projection based update method, which often require updating the full image at each step. Alternatively multiple voxels can be updated simultaneously using a block-based inversion technique or using a Jacobi update step.

With the knowledge of the local motion map (see e.g., reference to motion locations 312-318 of FIG. 4, or step 408 of FIG. 5), voxels of the selected image (e.g., either a first image based on a first subset of the CT data or the second image based on the second subset of the CT data) can be iteratively updated only in regions where motion has been identified. As such, computational requirements are reduced by focusing computation to areas that may contain motion artifacts.

Multiple models may be employed for temporal regularization. For example, according to one model, temporal regularization is added by penalizing the difference between the most recent updated data and non-temporally-resolved data, $\tilde{x}$, that may be blurred, or include motion artifacts. In such a model, the cost function may be represented as follows:

$$U_t(x) = \Sigma_j (x_j - \tilde{x}_j)^p, \text{ with } 1 \le p \le 2 \quad \text{(Eqn. 4).}$$

where $\tilde{x}$ may be formed using a full-scan or a complete half-scan over "y," and the iterative reconstruction can be performed using less than a half-scan, where $y \subset \tilde{y}$, and using the temporal regularization to stabilize the solution. Compared to a quadratic penalty with p=2, the absolute difference function associated with p=1, and also called the L1-norm, may help localize the changes to the updated regions where motion is taking place.

That illustrated above with respect to FIGS. 2-8 is specific to embodiments of the invention as related to a CT system. However, as stated, the invention is applicable to other imaging modalities, some of which include SPECT, PET, and various baggage scanner modalities, as just a few examples.

Figure 9:
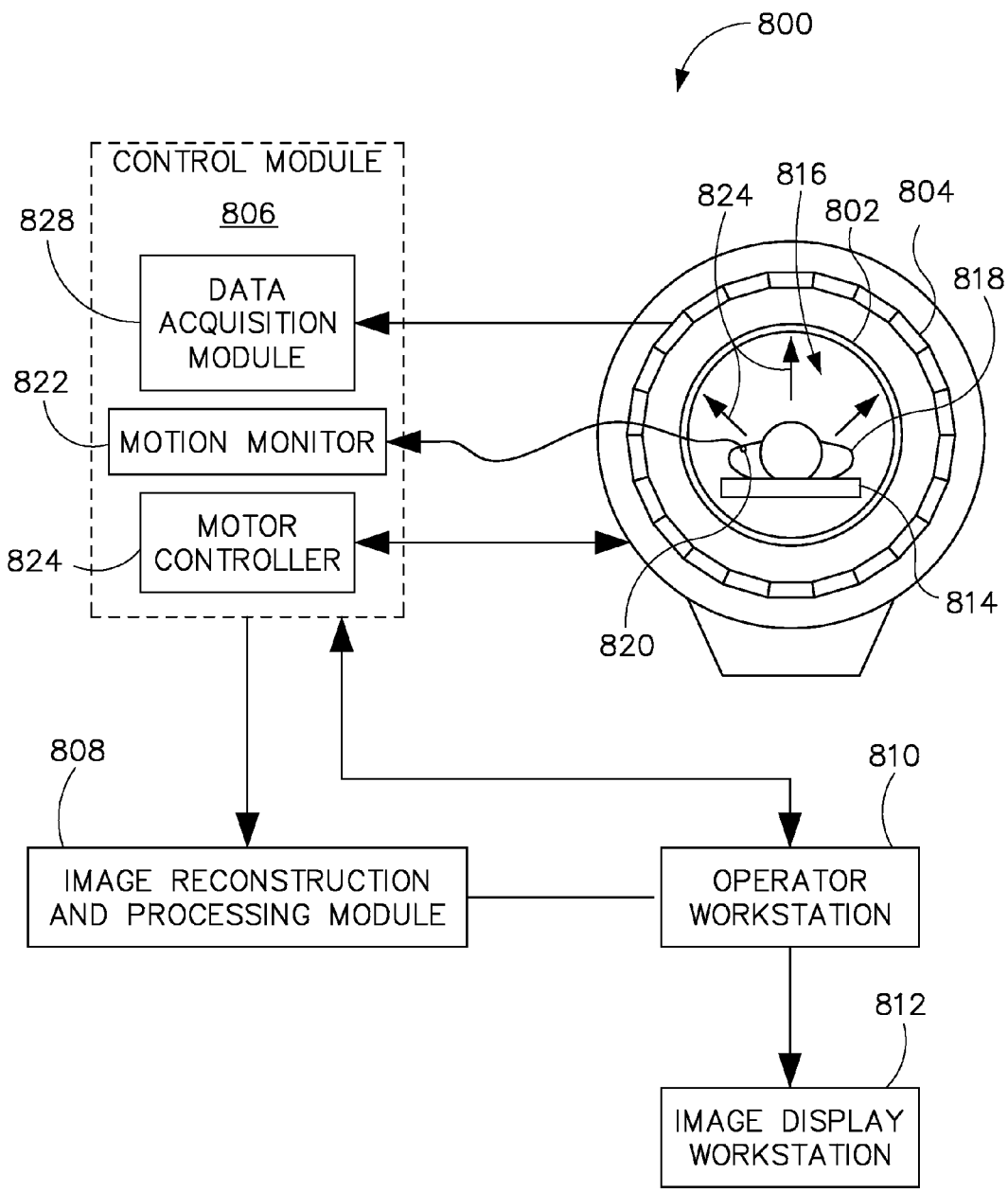
FIG. 9 is a pictorial view of a SPECT imaging system incorporating embodiments of the invention.

FIG. 9 illustrates an exemplary SPECT system 800 for acquiring and processing image data in accordance with embodiments of the invention. SPECT system 800 includes a collimator assembly 802 and a detector assembly 804. SPECT system 800 also includes a control module 806, an image reconstruction and processing module 808, an operator workstation 810, and an image display workstation 812.

As illustrated, a subject support 814 (e.g., a table) may be moved into position in a field-of-view (FOV) 816 of SPECT system 800. In the illustrated embodiment, subject support 814 is configured to support a subject 818 (e.g., a human patient, a small animal, a plant, a porous object, etc.) in position for scanning Alternatively, subject support 814 may be stationary, while SPECT system 800 may be moved into position around subject 818 for scanning. Subject 818 may be supported in any suitable position for scanning. In one example, subject 818 may be supported in FOV 816 in a generally vertical position, a generally horizontal position, or any other suitable position (e.g., inclined) for the desired scan. In another example, subject 818 may have a motion monitoring system 820, such as an ECG, attached thereto and connected to a motion monitor 822 within control module 806. Thus, motion monitoring system 820 may be controlled and used to obtain patient motion information such as respiratory and cardiac phase information, as examples.

In SPECT imaging, subject 818 is typically injected with a solution that contains a radioactive tracer. The solution is distributed and absorbed throughout subject 818 in different degrees, depending on the tracer employed and, in the case of living subjects, the functioning of the organs and tissues. The radioactive tracer emits electromagnetic rays 824 (e.g., photons or gamma quanta) known as "gamma rays" during a nuclear decay event.

Collimator assembly 802 receives gamma rays 824 emanating from FOV 816. Collimator assembly 802 is generally configured to limit and define a direction and angular divergence of gamma rays 824. In general, collimator assembly 802 is disposed between detector assembly 804 and FOV 816. Gamma rays 824 that pass through collimator assembly 802 impact detector assembly 804. Due to collimation of gamma rays 824 by collimator assembly 802, detection of gamma rays 824 may be used to determine a line of response along which each ray of gamma rays 824 travels before impacting detector assembly 804, allowing localization of an origin for each gamma ray to that line. In general, detector assembly 804 may include a plurality of detector elements configured to detect gamma rays 824 emanating from subject 818 in FOV 816 and passing through one or more apertures defined by collimator assembly 802. In exemplary embodiments, each of the plurality of detector elements in detector assembly 804 produces an electrical signal in response to the impact of the gamma rays 824.

The detector elements may be arranged in detector assembly 804 in any suitable manner. Detector assembly 804 may extend at least partially around FOV 816. In certain embodiments and as illustrated, detector assembly 804 may include modular detector elements arranged around FOV 816. Alternatively, detector assembly 804 may be arranged in a ring that may extend up to 360° around FOV 816. In certain embodiments, detector assembly 804 may extend from about 180° to about 360° around FOV 816.

To acquire multiple lines of response emanating from subject 818 in FOV 816 during a scan, collimator assembly 802 may be configured to rotate about subject 818 positioned within FOV 816. In one example, collimator assembly 802 may be configured to rotate with respect to detector assembly 804. Detector assembly 804 may be stationary while collimator assembly 802 may be configured to rotate about FOV 816. Alternatively, detector assembly 804 may rotate while collimator assembly 802 is stationary. In another example, collimator assembly 802 and detector assembly 804 may both be configured to rotate, either together or independently of one another. Alternatively, if sufficient pinhole apertures and/or slit apertures are provided through collimator assembly 802 or if the slit apertures are orthogonal to the longitudinal axis of collimator assembly 802, then no rotation may be required.

In the illustrated embodiment, control module 806 includes a motor controller 826 and a data acquisition module 828. In general, gantry motor controller 826 may control a rotational speed and position of collimator assembly 802, detector assembly 804, and/or a position of subject support 814. Data acquisition module 828 may be configured to obtain signals generated in response to impact of gamma rays 824 with detector assembly 804. For example, data acquisition module 828 may receive sampled electrical signals from detector assembly 804 and convert the data to digital signals for subsequent processing by image reconstruction and processing module 808. Any suitable technique for data acquisition may be used with SPECT system 800. In examples, and as understood in the art, the data needed for image reconstruction may be acquired in a list or a frame mode. Data may be acquired, parsed, and reconstructed according to embodiments of the invention.

Steps of technique 100 as discussed with respect to FIG. 1 may be applied to a SPECT system to obtain and reconstruct a working image from imaging data according to an embodiment of the invention. A minimum SPECT dataset may be obtained of an object such as a heart within patient 818 as illustrated above in FIG. 8. According to embodiments of the invention, gantry speed is relatively slow compared to CT system 200 described above and is in terms of minutes (as opposed to sub-second gantry rotation in typical CT imaging). To improve resolution according to an embodiment of the invention, data is acquired in one embodiment for a 10 minute period and over 180° of rotation, since parallel hole collimation can be used and as understood in the art. Using the techniques described above, only a fraction of the acquired dataset is then used for the final image production. The fraction of the acquired dataset is defined temporally (that is, using a subset of acquired data having a desired temporal distribution). A working image is reconstructed and one or more motion regions is identified either using projection data obtained outside the temporal window (as described with respect to FIG. 4) or by using offset scan datasets (as described with respect to FIGS. 7 and 8). Alternatively, the data acquisition can be divided into two steps. In the first step, projections over 180° (for parallel collimation) or 180° (for fan-beam or cone-beam collimator) are quickly collected. Next, a pinhole collimator is used to acquire the projections simultaneously over a limited angular range while the gantry is stationary. Since the projection data is acquired at the same time (without gantry rotation), the data acquisition can be effectively gated by the physiological signals such as ECG. The projections acquired with the pinhole collimator are used for the iterative reconstruction to refine the working image.

Figure 10:
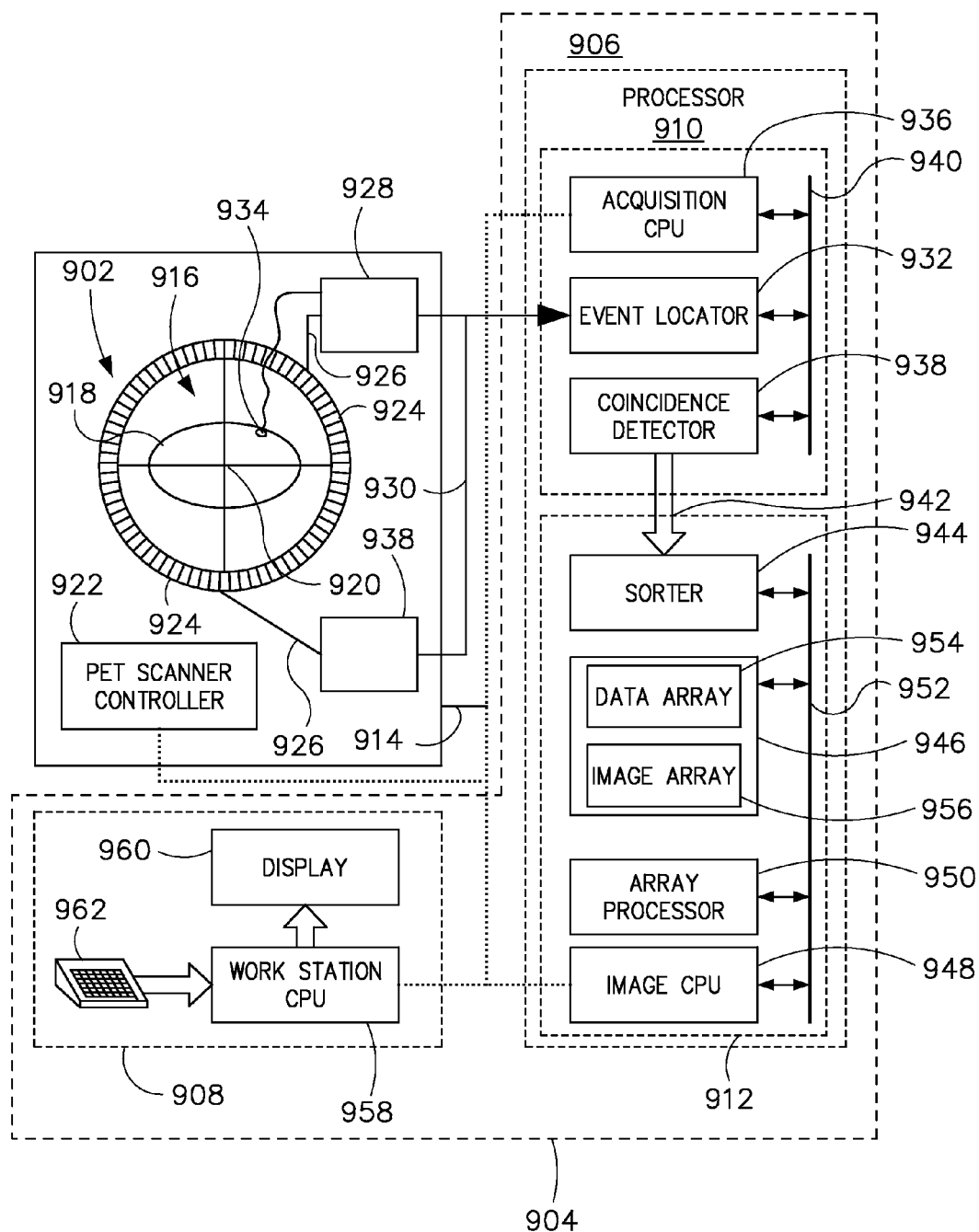
FIG. 10 is a pictorial view and block diagram of a PET system incorporating embodiments of the invention.
Figure 11:
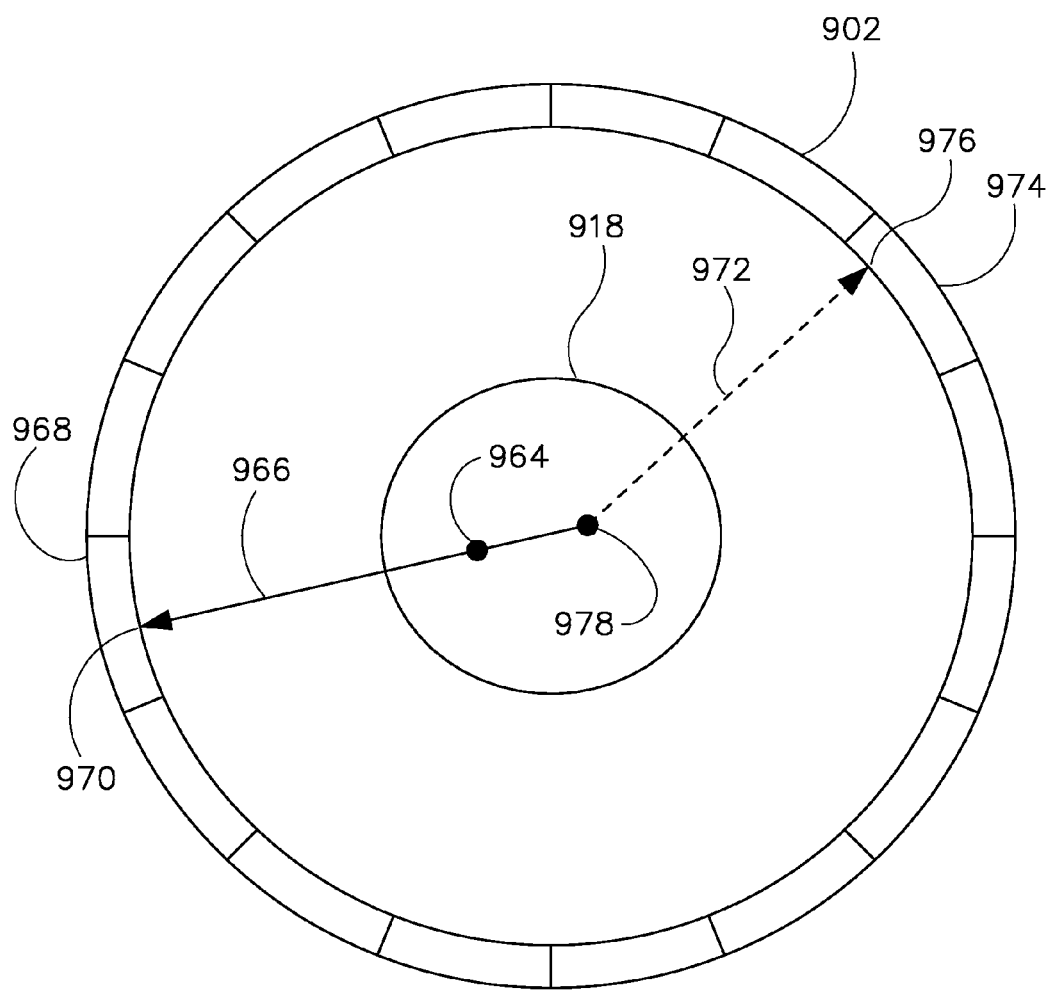
FIG. 11 is a view of a detector ring of the PET system of FIG. 10.

FIG. 10 is a block diagram of an exemplary embodiment of a PET system 900 in which various embodiments of the invention may be implemented. PET system 900 includes a plurality of detector ring assemblies. One such detector ring assembly, detector ring assembly 902, is illustrated in FIG. 11. PET system 900 further includes a controller 904 to control normalization and image reconstruction processes. Controller 904 includes a processor 906 and an operator workstation 908. Processor 906 includes a data acquisition processor 910 and an image reconstruction processor 912 that are interconnected and connected with detector ring assembly 902 via a communication link 914. PET system 900 acquires scan data and transmits the data to data acquisition processor 910. The scanning operation is controlled from operator workstation 908. The data acquired by data acquisition processor 910 is reconstructed using image reconstruction processor 912.

Detector ring assembly 902 includes a central opening 916 in which a patient or object 918 may be positioned using, for example, a motorized table (not shown) that is aligned with a central axis 920 of detector ring assembly 902. The motorized table moves object 918 into central opening 916 of detector ring assembly 902 in response to one or more commands received from operator workstation 908. A PET scanner controller 922, also referred to as the gantry controller, is provided (e.g., mounted) within PET system 900. PET scanner controller 922 responds to commands received from operator workstation 908 through communication link 914.

Detector ring assembly 902 includes a plurality of detector units 924 (e.g., in one known PET system, there are 420 crystals per ring, and 24 rings in the scanner). While not shown, it is contemplated that each detector unit 924 includes a set of scintillator crystals arranged in a matrix disposed in front of a plurality of photomultiplier tubes (e.g., four tubes). When a photon collides with a scintillator crystal on a detector unit 924, it produces a scintilla on the scintillator crystal. Each photomultiplier tube produces an analog signal on a communication line 926 when a scintillation event occurs. A set of acquisition circuits 928 is provided to receive these analog signals. Acquisition circuits 928 produce digital signals indicating a location in 3-dimensional (3D) space and a total energy of the event. Acquisition circuits 928 also produce an event detection pulse, which indicates the time or moment the scintillation event occurred. These digital signals are transmitted through a communication link 930 such as a cable, for example, to an event locator circuit 932 in data acquisition processor 910. In one embodiment, PET system 900 includes a motion monitoring system 934, such as an ECG, attached to object 918 and attached to acquisition circuit 928 that may be used to obtain patient motion information such as respiratory and cardiac phase information, as examples, via data acquisition processor 910.

Data acquisition processor 910 includes event locator circuit 932, an acquisition CPU 936 and a coincidence detector 938. Data acquisition processor 910 periodically samples the signals produced by acquisition circuits 928. Acquisition CPU 936 controls communications on a back-plane bus 940 and on communication link 914. Event locator circuit 932 processes information regarding each valid event and provides a set of digital numbers or values indicative of the detected event. For example, this information indicates when the event took place and the position of the scintillation crystal that detected the event. An event data packet (not shown) containing the event information is communicated to coincidence detector 938 through back-plane bus 940. Coincidence detector 938 receives the event data packets from event locator circuit 932 and determines if any two of the detected events are in coincidence. Coincidence is determined by a number of factors. First, time markers in each event data packet should be within a predetermined time period of each other such as, for example, 12.5 nanoseconds. Second, a line of response (LOR) formed by a straight line joining the two detectors that detect the coincidence event should pass through the central opening 916 or through a field of view in PET system 900. Events that cannot be paired are discarded. Coincident event pairs are located and recorded as a coincidence data packet that is communicated through a communication link 942 to a sorter 944 in image reconstruction processor 912.

Image reconstruction processor 912 includes sorter 944, a memory module 946, an image CPU 948, an array processor 950 and a back-plane bus 952. Sorter 944 counts all events occurring along each projection ray and organizes them into 3D data. This 3D data (or sinograms) is organized, in one exemplary embodiment, as a data array 954. Data array 954 is stored in memory module 946. Back-plane bus 952 is linked to communication link 914 through image CPU 948, and image CPU 948 controls communication through back-plane bus 952. Array processor 950 is also connected to back-plane bus 952. Array processor 950 receives data array 954 as an input and reconstructs images in the form of image arrays 956. Resulting image arrays 956 are stored in memory module 946.

Images stored in image arrays 956 are communicated by image CPU 948 to operator workstation 908. Operator workstation 908 includes a CPU 958, a display device 960 and an input device 962. Acquisition CPU 958 connects to communication link 914 and receives inputs (e.g., user commands) from input device 962. Input device 962 may be, for example, a keyboard, mouse, or a touch-screen panel. Through input device 962 and associated control panel switches, an operator can control calibration of PET system 900 and can control positioning of object 918 for a scan. Similarly, an operator can control display of a resulting image on display device 960 and perform image-enhancement functions using programs executed by acquisition CPU 958.

The data array received by array processor 950 may be corrected for errors before being reconstructed. The level of correction may be based on, for example, a desired resolution level for a reconstructed image. One correction includes removing scatter coincidences from the image data.

FIG. 11 illustrates a single scatter coincidence with respect to detector ring assembly 902 of FIG. 10. An annihilation event occurs at an annihilation point 964 inside object 918. The annihilation event produces a photon 966 that impacts a detector element 968 at a first detection point 970, and a scattered photon 972 that impacts a detector element 974 at a second detection point 976. Scattered photon 972 is scattered from a scattering point 978 inside object 918. Detector element 968 records a time at which photon 966 is detected and a time at which scattered photon 972 is detected. Detector element 968 and detector element 974 form a detector pair. As known in the art, detector element pair 968/974 map to a unique sinogram bin with indices, r and θ, and indices r and θ denote a radial distance from the center of the detector ring and an angle of the line joining 968 and 976 from a horizontal axis, respectively. A difference between detection times for first detection point 970 and second detection point 976 maps to a unique time bin index for the time-of-flight scatter sinogram. For each of the plurality of detector pairs, the total number of annihilation events and the time at which each event is recorded is sent to processor 906 (shown in FIG. 11). Based on the received information, the detected events are binned into sinograms with indices r and θ, used to generate a time-of-flight scatter sinogram S(r, θ, t).

Imaging data is obtained and reconstructed using the PET system illustrated with respect to FIGS. 10 and 11 and according to technique 100 described with respect to FIG. 1 above. According to this embodiment, a PET dataset is obtained of an object, such as a heart within patient or object 918 as illustrated above in FIG. 10. According to the invention, a conventional PET dataset may be obtained (e.g., over a 5 minute period) and used to generate a working image. A region of motion is identified and revised as discussed above. One or more motion regions is identified either using projection data obtained outside the temporal window (as described with respect to FIG. 4) or by using offset scan datasets (as described with respect to FIGS. 7 and 8).

Data collected over a fractional period of time (i.e., a defined temporal window) may then be used to refine the working image to remove motion. A quiescent time period may be selected within the original acquisition window (5 minutes, in this example) to iteratively produce a final or refined image. Thus, the final image exhibits the noise property of the longer scan time (e.g., 5 minutes) but exhibits the motion property of an improved temporal window. As such, and as described, a conventional or normal PET dataset is obtained, and a fraction of the acquired dataset is defined temporally.

Figure 12:
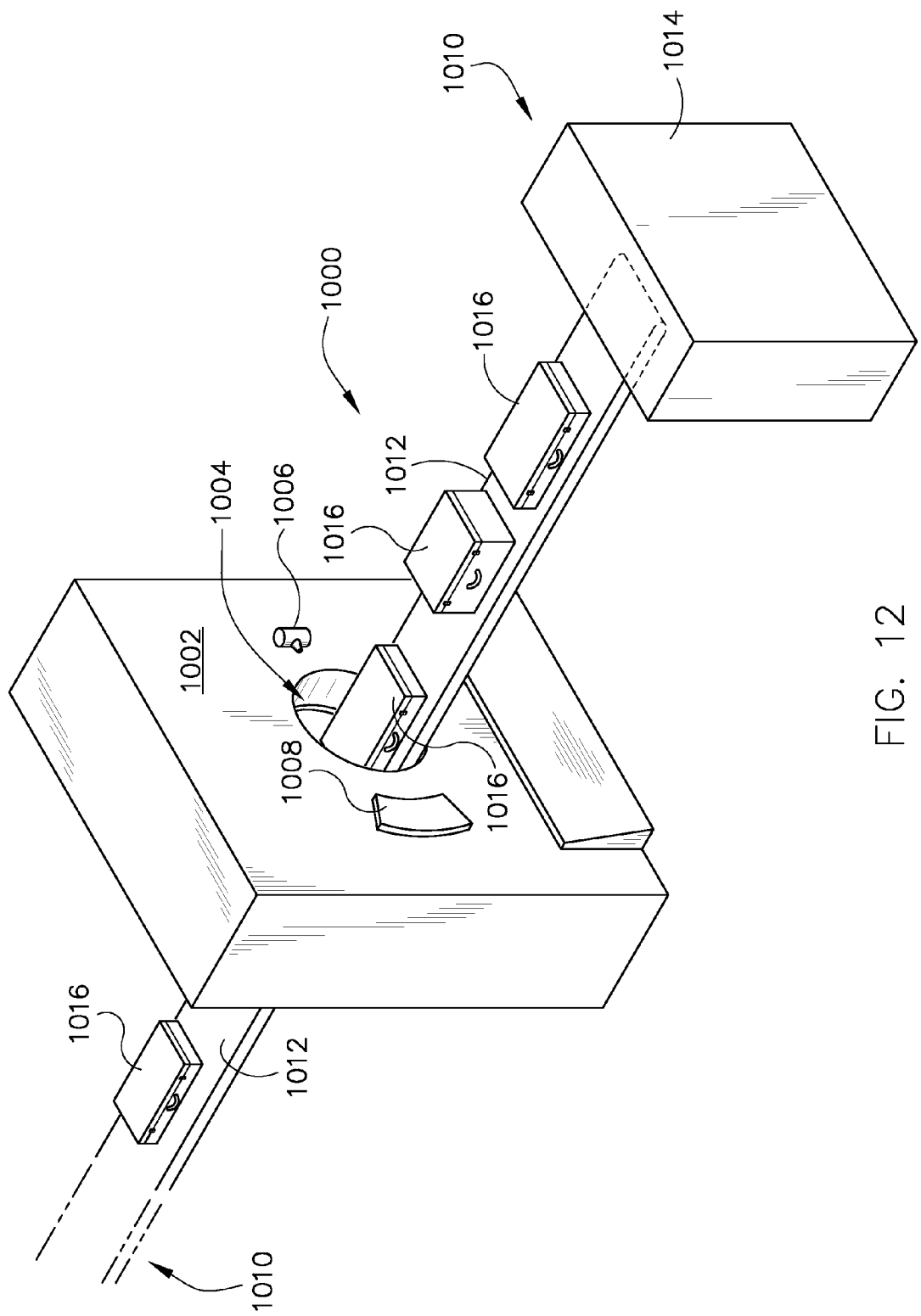
FIG. 12 is a pictorial view of a baggage scanning system incorporating embodiments of the invention.

Referring now to FIG. 12, there is shown a package/baggage inspection system 1000 that can use the data acquisition technique according to embodiments of the invention and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of embodiments of the invention in an example comprises a plurality of components such as one or more of electronic components, hardware components, and/or computer software components. A number of such components can be combined or divided in an implementation of the embodiments of the invention. An exemplary component of an implementation of the embodiments of the invention employs and/or comprises a set and/or series of computer instructions written in or implemented with any of a number of programming languages, as will be appreciated by those skilled in the art.

An implementation of the embodiments of the invention in an example employs one or more computer readable storage media. An example of a computer-readable signal-bearing medium for an implementation of the embodiments of the invention comprises the recordable data storage medium of the image reconstructor 34, and/or the mass storage device 38 of the computer 36. A computer-readable storage medium for an implementation of the embodiments of the invention in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory.

According to one embodiment of the invention, a tomographic system includes a gantry having an opening for receiving an object to be scanned, a radiation source, a detector positioned to receive radiation from the source that passes through the object, and a computer. The computer is programmed to acquire a plurality of projection datasets of the object, define a temporal subset of projection datasets from the plurality of projection datasets, reconstruct a working image of the object using the plurality of projection datasets, identify a region of motion in the working image, and minimize motion artifacts in the region of motion in the working image using the temporal subset of projection datasets.

According to another embodiment of the invention, a method of image reconstruction includes obtaining a plurality of projection datasets of an object, defining a temporal subset of projection datasets from the plurality of projection datasets, reconstructing an image of the object using the plurality of projection datasets, and correcting a motion artifact in at least one identified voxel of the image using the temporal subset of projection datasets.

According to yet another embodiment of the invention, a computer readable storage medium having stored thereon a computer program comprising instructions, which, when executed by a computer, cause the computer to access a plurality of tomographic view datasets of an object, identify a temporal subset of the plurality of tomographic view datasets, reconstruct a processing image of the object using the plurality of tomographic view datasets, and revise at least one image voxel in an identified region of motion of the processing image using at least one tomographic view dataset of the temporal subset of tomographic view datasets.

A technical contribution for the disclosed method and apparatus is that it provides for a computer-implemented apparatus and method of acquiring tomographic imaging data and increasing temporal resolution of a tomographic image.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A tomographic system comprising:
   a gantry having an opening for receiving an object to be scanned;
   a radiation source;
   a detector positioned to receive radiation from the source that passes through the object; and
   a computer programmed to:
   acquire a plurality of projection datasets of the object;
   define a temporal subset of projection datasets from the plurality of projection datasets;
   reconstruct a working image of the object using the plurality of projection datasets;
   identify a region of motion in the working image; and
   minimize motion artifacts in the region of motion in the working image using the temporal subset of projection datasets.

2. The tomographic system of claim 1 wherein the computer is programmed to identify the region of motion in the working image using one of: the plurality of projection datasets, projection datasets obtained outside of the defined temporal window, and a motion map generated using at least the working image.

3. The tomographic system of claim 1 wherein the computer is programmed to acquire the plurality of projection datasets of the object over a half-scan of the object.

4. The tomographic system of claim 1 wherein the computer is programmed to define the temporal subset of projection datasets using an electrocardiograph (ECG).

5. The tomographic system of claim 1 wherein the computer is programmed to define the temporal subset of projection datasets as projection datasets acquired over 90° or more of a rotation of the gantry.

6. The tomographic system of claim 1 wherein the computer is programmed to define the temporal subset of projection datasets based on a temporal feature of the object.

7. The tomographic system of claim 1 wherein the computer is programmed to define the temporal subset of projection datasets as projection datasets acquired over 130° or less of a rotation of the gantry.

8. The tomographic system of claim 1 wherein the computer is programmed to identify the region of motion of the working image using one of projection datasets from two or more radiation source positions and a difference image that is generated using a first image and a second image.

9. The tomographic system of claim 1 wherein the computer is programmed to correct the identified region of motion using a projection dataset from the plurality of projection datasets that is not a projection dataset of the defined temporal subset of projection datasets.

10. The tomographic system of claim 1 wherein the computer is programmed to reconstruct the working image of the object using one of a model-based iterative reconstruction (MBIR), an algebraic reconstruction technique (ART), a simultaneous algebraic reconstruction technique (SART), an ordered subset expectation maximization (OSEM), and a kinetic parameter iterative reconstruction (KPIR).

11. The tomographic system of claim 1 wherein the gantry is one of a computed tomography (CT) gantry, a c-arm gantry, a PET gantry, and a SPECT gantry.

12. A method of image reconstruction comprising:
   obtaining a plurality of projection datasets of an object;
   defining a temporal subset of projection datasets from the plurality of projection datasets;
   reconstructing an image of the object using the plurality of projection datasets; and
   correcting a motion artifact in at least one identified voxel of the image using the temporal subset of projection datasets.

13. The method of claim 12 comprising identifying the voxel in the image that includes a motion artifact using the plurality of projection datasets.

14. The method of claim 12 wherein obtaining the plurality of projection datasets comprises obtaining a half-scan of projection datasets.

15. The method of claim 12 comprising obtaining electrocardiograph (ECG) data of the object and wherein defining the temporal subset of projection datasets comprises defining the temporal subset of projection datasets using the ECG data.

16. The method of claim 12 wherein defining the temporal subset of projection datasets comprises defining the temporal subset of projection datasets as projection datasets obtained over 90° or greater of a rotation of a gantry.

17. The method of claim 12 wherein defining the temporal subset of projection datasets comprises defining the temporal subset of projection datasets as projection datasets obtained based on a temporal feature of the object.

18. The method of claim 12 wherein defining the temporal subset of projection datasets comprises defining the temporal subset of projection datasets as projection datasets obtained over 130° or less of a rotation of a gantry.

19. The method of claim 12 comprising identifying the voxel in the image that includes the motion artifact using two or more projection datasets from the plurality of projection datasets that are not included in the temporal subset of projection datasets.

20. The method of claim 12 comprising identifying the voxel in the image that includes the motion artifact using a difference image that is generated using a first reconstructed image and a second reconstructed image.

21. The method of claim 12 comprising correcting the motion artifact of the identified voxel of the image using one or more projection datasets of the plurality of projection datasets that are not part of the temporal subset of projection datasets.

22. The method of claim 12 comprising reconstructing the image of the object using one of a model-based iterative reconstruction (MBIR), an algebraic reconstruction technique (ART), a simultaneous algebraic reconstruction technique (SART), an ordered subset expectation maximization (OSEM), and a kinetic parameter iterative reconstruction (KPIR).

23. A computer readable storage medium having stored thereon a computer program comprising instructions, which, when executed by a computer, cause the computer to:

access a plurality of tomographic view datasets of an object;

identify a temporal subset of the plurality of tomographic view datasets;

reconstruct a processing image of the object using the plurality of tomographic view datasets; and revise at least one image voxel in an identified region of motion of the processing image using at least one tomographic view dataset of the temporal subset of tomographic view datasets.

24. The computer readable storage medium of claim 23 wherein the instructions that cause the computer to access the plurality of tomographic view datasets cause the computer to access the plurality of tomographic view datasets along a circumference of a gantry rotational arc.

25. The computer readable storage medium of claim 23 wherein the instructions further cause the computer to identify the region of motion in the processing image using the plurality of tomographic view datasets.

26. The computer readable storage medium of claim 23 wherein the instructions further cause the computer to access the plurality of tomographic view datasets of the object such that a half-scan tomographic view dataset is formed.

27. The computer readable storage medium of claim 23 wherein the instructions further cause the computer to identify the temporal subset of tomographic view datasets based on temporal features of the object.

28. The computer readable storage medium of claim 23 wherein the instructions further cause the computer to identify the temporal subset of tomographic view datasets to be between approximately 90° and 130° of a rotation of a gantry rotational arc.

29. The computer readable storage medium of claim 23 wherein the instructions further cause the computer to identify the region of motion using a difference image that is generated using at least the processing image.

30. The computer readable storage medium of claim 23 wherein the instructions further cause the computer to revise the at least one image voxel using the plurality of tomographic view datasets of the object.

* * * * *